United States Patent [19]

Slamon et al.

[11] Patent Number: 5,063,150

[45] Date of Patent: Nov. 5, 1991

[54] RETROVIRAL POLYPEPTIDES ASSOCIATED WITH HUMAN CELLULAR TRANSFORMATION

[75] Inventors: Dennis J. Slamon, Woodland Hills; Irvin S. Y. Chen, Sherman Oaks, both of Calif.

[73] Assignee: The Regents of The University of California, Berkeley, Calif.

[21] Appl. No.: 86,088

[22] PCT Filed: Sep. 19, 1985

[86] PCT No.: PCT/US85/01803

§ 371 Date: Nov. 13, 1987

§ 102(e) Date: Nov. 13, 1987

[87] PCT Pub. No.: WO86/01834

PCT Pub. Date: Mar. 27, 1986

[51] Int. Cl.$^5$ .......................................... G01N 33/569
[52] U.S. Cl. .......................................... 435/5; 435/7.1; 530/324; 530/325; 530/326; 530/387; 530/395; 530/826
[58] Field of Search ................. 435/5, 7; 530/324–328, 530/387, 395, 826

[56] References Cited

U.S. PATENT DOCUMENTS 4,311,639  1/1982  Ganfield et al. ............. 260/112.5 R
4,341,761  7/1982  Ganfield et al. ....................... 424/85
4,384,995  5/1983  Stevens ........................ 260/112.5 R
4,407,965 10/1983  Yanaihara ............................ 436/547
4,423,034 12/1983  Nakagawa et al. ..................... 424/85
4,438,030  3/1984  Ganfield et al. ...................... 424/85
4,520,113  5/1985  Gallo et al. ............................. 435/5

FOREIGN PATENT DOCUMENTS 8403506  9/1984  PCT Int'l Appl. ...................... 435/5

OTHER PUBLICATIONS

Walter, G. et al., Proc. Natl. Acad. Sci. U.S.A., 78(8):4882–4886 (8–1981).
Hopp, T. P. et al., Proc. Natl. Acad. Sci., U.S.A., 78(6):3824–3828 (6–1981).
Baron, M. H. et al., Cell, 28:395–404 (2–1982).
Pfaff, E. P. et al., EMBO Journal, 1(7):869–874 (7–1982).
Lerner, R. A., Nature, 299:592–596 (10–1982).
Sen, S. et al., Proc. Natl. Acad. Sci., U.S.A., 80:1246–1250 (3–1983).
Boyle, W. J. et al., Proc. Natl. Acad. Sci., U.S.A., 80:2834–2838 (5–1983).
Sutcliffe, J. G. et al., Cell, 33:671–682 (7–1983).
Tamura, T. et al., Cell, 34:587–596 (9–1983).
Lee, T. H. et al., *Human T-Cell Leukemia/Lymphoma Virus*, Cold Spring Harbor, N.Y., (1984), Gallo, R. C. et al., eds. pp. 111–120, Meeting date Sep. 14–16, 1983.
Seiki, M. et al., Proc. Natl. Acad. Sci., U.S.A., 80:3618–3622 (6–1983) cited in Bio Abstract 77010920.
Chen, I. S. Y. et al., Science, 229:54–58 (1985).
Haseltine, W. A. et al., Science, 225:419–421 (1984) cited in Bio. Abstract 78083272.
Sodroski, J. et al., Proc. Natl. Acad. Sci., U.S.A., 81:4617–4621 (1984).
Lee, T. H. et al., Science, 226:57–61 (10–1984).
Slamon, D. J. et al., Science, 226:61–65 (10–1984).
Wachsman, W. et al., Science, 226:177–179 (10–1984).
Koeffler, H. P. et al., Blood: 482–490 (8–1984).
Marx, J. L., Science, 225:398–399 (7–1984).
Sodroski, J. G. et al., Science, 225:381–385 (7–1984).
Shaw, G. M. et al., P.N.A.S. 81:4544–4548 (7–1984).
Watanabe, T. et al., Virology, 133:238–241 (2–1984).
Popovic, M. et al., Science, 219:856–859 (2–1983).
Kalyanaraman, V. S. et al., Science, 218:571–573 (11–1982).
Hinuma, Y. et al., Proc. Natl. Acad. Sci., U.S.A., vol. 78(10): 6476–6480 (10–1981).
Poiesz, B. J. et al., Proc. Natl. Acad. Sci., U.S.A., vol. 77(12): 7415–7419 (12–1980).
Sodroski, J. et al., Science 228:1430–1434 (6–1985).
Wachsman, W. et al., Science, 228:1534–1537 (6–1985).
Goh, W. C. et al., Science 227:1227–1228 (3–1985).
Shimotohno, K. et al., Proc. Natl. Acad. Sci., U.S.A., 81(4):1079–1083 (1984), cited in Chem. Abstract 100(23):186546u.
Ratner, L. et al., Nature 313:277–284 (1985).
Miwa, M. et al., GANN 75(9):752–755 (1984), cited in Chem. Abst. 101(21):187639j.
Shimotohno, K. et al., Proc. Natl. Acad. Sci., U.S.A., 81(21): 6657–6661 (10–1984), cited in Bio. Abst. 79058183.
Sagata, N. et al., EMBO J., 3(13):3231–3238 (1984), cited in Bio. Abstract 79076558.
Yamaguchi, K. et al., Blood 63(5):1235–1240 (1984), cited in Bio. Abstract 78052685.
Hahn, B. H. et al., Symposia on Molecular Cellular Biology, 16:73–82 (1984), (Conference, Utah, U.S.A., Feb. 5–10–1984), cited in Bio. Abstract 28043731.
Marx, J. L., Science, 229:37–38 (7–1985).

*Primary Examiner*—Christine Nucker
*Attorney, Agent, or Firm*—Barbara Rae-Venter; Bertram I. Rowland

[57] ABSTRACT

Polypeptides, fragments thereof, antisera and monoclonal antibodies thereto are provided for the detection of retroviruses in the HTLV family capable of inducing transformation in human lymphocytes and other immune cells, regulation of viral replication and transformation or infection of human cells.

27 Claims, No Drawings

RETROVIRAL POLYPEPTIDES ASSOCIATED WITH HUMAN CELLULAR TRANSFORMATION

BACKGROUND OF THE INVENTION

1. Field of the Invention

The recent discovery of retroviruses capable of infecting human lymphocytes, particularly T-cells, resulting in their transformation to lymphomas and leukemias offers insight into the etiology of these types of tumors. For the most part, transforming retroviral viruses observed with mammals other than humans had been divided into two groups: chronic transforming viruses, which integrate into the genome and are thought to lead to transformation by insertional mutagenesis, with activation of a cellular gene; and acutely transforming retroviruses which carry specific transforming sequences (viral oncogenes) which are related to cellular oncogenes or proto-oncogenes (Hayward et al., Nature (1981) 290:475; Nusse et al., Nature (1984) 307:131; Payne et al., Nature (1982) 295:209). However, the more recently discovered family of human T-lymphotropic viruses known as HTLV appear neither to integrate at specific sites nor have a viral oncogene with a normal cellular homolog. The mechanism of transformation by viruses in the HTLV family therefore appears to be different from other known retroviruses. The mechanism of action of viruses in the HTLV family is of interest since HTLV's have been connected with several devastating diseases. In particular, HTLV-I is associated with adult T-cell leukemia and HTLV-II has been isolated from a T-cell variant of hairy cell leukemia.

In order to be able to understand the mechanism of transformation or infection by viruses in the HTLV family to allow for diagnosis, therapy, and in vitro applications which allow for controlled transformation or infection of T-cells, it is of interest to determine the mechanism by which the viruses in the HTLV family transform or infect T-cells or other immune cells and then characterize and isolate compositions involved in the transformation or infection, as well as proliferation and growth cycle of the viruses.

2. Description of the Prior Art

The nucleotide sequences of HTLV-I and -II demonstrate a highly conserved region located between env and the 3' LTR of the virus, which finds its only analogy in a homologous sequence in bovine leukemia virus (Haseltine et al., Science (1984) 225:419). Seiki et al., Proc. Natl. Acad. Sci. USA (1983) 80:3618–3622, have reported four open reading frames in the X sequence of HTLV-I. Haseltine et al., Science (1984) 225:419, as well as Shimotohno et al., Proc. Natl. Acad. Sci. USA (1984) 81:1079–1083, report that there are three open reading frames in a region referred to as the X sequence of HTLV-II. Comparison of the nucleotide sequences of the X regions from the two viruses reveals significant sequence homology (about 75%) between the pX-IV region of HTLV-I and the pX-c region of HTLV-II. More recent data has shown that the amount of homology at the nucleotide level is minimal between the genome of HTLV-III and the genomes of the other viruses in the HTLV series.

SUMMARY OF THE INVENTION

Polypeptides and antibodies thereto are provided, where the polypeptides are associated with immunogenic sites involving expression products of viruses in the HTLV family, particularly HTLV-I and HTLV-II. The polypeptides and fragments thereof are related to the expression products of the X region of an HTLV virus and can be used as immunogens for the production of antisera or monoclonal antibodies specific for the epitopic sites. The polypeptides and antibodies may be used as reagents in diagnosis, for the proliferation of the viruses, in transformation or infection of T-cells and other immune cells, and in the investigation of the etiology of cell transformation or infection by these retroviruses. In particular, the polypeptides may be used in the detection of anti-X region protein antibodies which have been demonstrated herein to be associated with exposure to and/or infection with HTLV.

DESCRIPTION OF THE SPECIFIC EMBODIMENTS

Novel polypeptides are provided which are the expression products of the X regions of viruses in the HTLV family or fragments thereof or fusion products of such polypeptides or fragments. Both the polypeptides and the antibodies may serve as immunogens for the production of polyclonal antisera or monoclonal antibodies. These materials may serve as reagents in diagnostic assays, in the regulation of growth of HTLV, in the transformation or infection of T-cells or other immune cells, as well as in the investigation of the etiology of cellular transformation by HTLV viruses.

HTLV as used in the specification and claims herein is intended to connote retroviruses capable of infecting human T-cells and other immune cells, having substantial homology with HTLV-I or -II ($\geq 40\%$), and having in the viral genome the structural genes gag, pol, and env, and well as 5'- and 3'-LTR's and an X sequence, preferably having an X region or sequence between the env and 3'-LTR, which encodes a protein expressed by the virus.

Proteins expressed by the X region of HTLV typically have a molecular weight in the range of about 35 kd to about 42 kd, depending on the specific virus and infected organism or cell line employed. More usually, the proteins encoded by X region of HTLV range from about 37 kd to about 40 kd in molecular weight. In particular, the polypeptides encoded for in the region described as pX-IV in the X sequence of HTLV-I and the region described as pX-c in the X sequence of HTLV-II are characterized by being respectively about 40 kd and 37 kd. For convenience, they will be referred to respectively as $p40^{xI}$ and $p37^{xII}$.

These polypeptides are further characterized by having at least one sequence of 12 amino acids which comes within any of sequences 1 through 4 shown below, preferably having at least 14 amino acids which come within these sequences, and more preferably having at least portions of two or more of the sequences, where the higher numbered sequences are closer to the N-terminus.

Sequence (1): C P E H Q (aa)$^A$ T W D P I D G R

Sequence (2): I P R L P S F P T Q R T S (aa)$^B$ T L K

Sequence (3): K(aa)$^{ArB}$ (aa)$^{Ah}$ P (aa)$^{Ar}$ RNG (aa)$^{ArS}$ (aa)$^{AS}$ EPTLG (aa)$^{AcAm}$ (aa)$^{AmB}$ LP (aa)$^{Ah}$ L (aa)$^{AAh}$ FP (aa)$^{Ac}$ PGLRPQN (aa)$^A$ YT (aa)$^{AAh}$ WG (aa)$^{AB}$ (aa)$^{Ah}$ VVC (aa)$^{AS}$ YLYQLSPP (aa)$^{AS}$ TWPL (aa)$^A$ PHVIFCHP (aa)$^{AB}$ Q Sequence (4): V (aa)$^A$ QSS (aa)$^{AAh}$ (aa)$^{AAr}$ IF (aa)$^{AcB}$ KF (aa)$^{AcAm}$ TKA (aa)$^{Ar}$ HPS (aa)$^{Ar}$ LLSH (aa)$^{AAm}$ LIQY SSFH (aa)$^{AhAm}$ LHLLF (aa)$^{Ac}$ EYTNIP (aa)$^A$ S (aa)$^A$ LFN (aa)$^{AcB}$ (aa)$^{AcB}$ EADDN (aa)$^{AAc}$ (aa)$^{AcB}$ EPQISPGGLEPPSEKH FRETEV quences which correspond to p37$^{xII}$(5A) and p40$^{xI}$(5B), respectively.

FIG. 1
Sequences 5A: p37$^{xII}$ (HTLV-II) and 5B: p40$^{xI}$ (HTLV-I)

| | | | | |
|---|---|---|---|---|
| (a) HTLV-II: | LQSCLLSAHFLG | FGQSLLYGYP | VYVFGDCVQA | |
| | ******* * | *** ** *** | ********* | |
| (b) HTLV-I: | --PCLLSAHFPG | FGQTLLFGYP | VYVFGDCVQG | |
| HTLV-II: | DPIDGRVVSS | PLQYLIPRLP | SFPTQRTSRT | |
| | ******* * | ** ****** | ***** ** * | |
| HTLV-I: | DPIDGRVIGS | ALQFLIPRLP | SFPTQTTSKT | |
| HTLV-II: | NGCLEPTLGD | QLPSLAFPEP | GLRPQNIYTT | |
| | ** ***** | ** * ** * | ****** ** | |
| HTLV-I: | NGYMEPTLGQ | HLPTLSFPDP | GLRPQNLYTL | |
| HTLV-II: | RQLGAFLTKV | PLKRLEELLY | KMFLHTGTVI | |
| | ******* * | * ** ***** | * ** * | |
| HTLV-I: | GQLGAFLTNV | PYKRIEELLY | KISLTTGALI | |
| HTLV-II: | YHSILTTPGL | IWTFNDGSPM | ISGPYPKAGQ | |
| | ** ****** | **** ** ** | **** ** ** | |
| HTLV-I: | FHSTLTTPGL | IWTFTDGTPM | ISGPCPKDGQ | |
| HTLV-II: | IQYSSFHNLH | LLFDEYTNIP | VSILFNKEEA | |
| | ******* ** | *** ****** | * *** ** | |
| HTLV-I: | IQYSSFHSLH | LLFEEYTNIP | ISLLFNEKEA | |
| (a) HTLV-II: | DWCPVSGGLC | STRLHRHALL | ATCPEHQLTW | 62 |
| | **** ***** | * ******** | ******* ** | |
| (b) HTLV-I: | DWCPISGGLC | SARLHRHALL | ATCPEHQITW | 60 |
| HTLV-II: | LKVLTPPTTP | VSPKVPPAFF | QSMRKHTPYR | 122 |
| | ******* * | * ** * | * *** * * | |
| HTLV-I: | LKVLTPPITH | TTPNIPPSFL | QAMRKYSPFR | 120 |
| HTLV-II: | WGKTVVCLYL | YQLSPPMTWP | LIPHVIFCHP | 182 |
| | ** *** ** | ****** *** | * ******** | |
| HTLV-I: | WGGSVVCMYL | YQLSPPITWP | LLPHVIFCHP | 180 |
| HTLV-II: | VLPEDDLPTT | MFQPVRAPCI | QTAWCTGLLP | 242 |
| | **** **** | *** *** | *** **** | |
| HTLV-I: | ILPEDCLPTT | LFQPARAPVT | LTAWQNGLLP | 240 |
| HTLV-II: | PSLVVQSSLL | IFEKFETKAF | HPSYLLSHQL | 302 |
| | **** *** | ** ** *** | *** **** * | |
| HTLV-I: | PSLVLQSSSF | IFHKFQTKAY | HPSFLLSHGL | 300 |
| HTLV-II: | DDNGD | | | 332 |
| | *** | | | |
| HTLV-I: | DDNDHEPQIS | PGGLEPPSEK | HFRETEV | 357 | wherein:

(aa)$^{xy}$ is an amino acid selected from the 20 naturally-occurring amino acids found in protein. The superscript(s) x,y indicate the nature of the preferred side chain on the amino acid, where

- A: aliphatic side chain, including glycine, alanine, valine, leucine, and isoleucine;
- Ac: acidic side chain, including aspartate and glutamate;
- Ah: aliphatic-hydroxyl side chain, including serine and threonine;
- Am: amide-containing side chain, including aspargine and glutamine;
- Ar: aromatic side chain, including histidine, phenylalanine, tyrosine, and tryptophan;
- B: basic side chain, including lysine, arginine, and histidine; and
- S: sulfur-containing side chain including cysteine and methionine.

In the polypeptides of interest which contain more than one of the above sequences, amino acid sequences 1 and 2 are separated by at least five amino acids, usually not more than twelve amino acids, typically by nine amino acids. Sequences 2 and 3 are separated by at least ten amino acids, usually by fewer than 30 amino acids, typically by 22 amino acids. Sequences 3 and 4 are separated by at least 20 amino acids, and may be separated by 200 or more amino acids, typically being separated by 91 amino acids.

These sequences may be joined together to form a larger polypeptide having either of the following sequences:

Preferred polypeptides (including oligopeptides and larger protein fragments) which represent antigenic epitopic sites in the expressions of the X region of HTLV in accordance with the invention include the following:

A: CPEHQITWDPIDGR
B: IPRLPSFPTQRTSKTLK
C: VLQSSSFIFG KFQTKAYHPS FLLSHGLIQY SSFHSLHLLF EEYTNIPISL LFNEKEADDN DHEPQISPGG LEPPSEKHFR ETEV
D: DNDHEPQISP GGLEPPSEK FRETEV

The foregoing polypeptides, and portions thereof, can be advantageously used as immunogens for the production of antisera or monoclonal antibodies specific for epitopic sites in the pX expression products of HTLV-I and -II and as reagents (labelled and unlabelled) to detect antibodies to the X region proteins of HTLV.

To be useful in the detection methods of the invention, the polypeptides of the invention are suitably obtained in substantially pure form, that is, typically about 50% w/w or more purity, substantially free of interfering proteins and contaminants. Preferably, these polypeptides are isolated or synthesized in a purity of at least about 80% w/w and, more preferably, in at least about 95% w/w purity, being substantially free of other proteins from humans, viral proteins, or other contaminants. Using conventional protein purification techniques, homogeneous polypeptides of at least about 99% w/w can be obtained; and these homogeneous polypeptides are most desirably used in the methods of the invention. In addition, the proteins of the invention can be obtained in substantially pure form by use of the antibodies herein described in immunoabsorbant affinity chromatography. This immunoabsorbant affinity chromatography is carried out by first linking the antibodies to a solid support and then contacting the linked antibodies with lysates of cells infected with one of the HTLV viruses. Proteins obtained in this manner are also within the scope of this invention and can be used in the methods of the invention to detect the presence of HTLV or its products.

The polypeptides greater than about 30 amino acids, particularly greater than about 50 amino acids may serve as immunogens or if less than about 10 kd, particularly less than about 6 kd, may be joined to other materials, particularly polypeptides, as fused or covalently joined polypeptides to be used as immunogens. The subject polypeptides may be fused or covalently linked to a variety of immunogens, such as keyhole limpet hemocyanin, bovine serum albumin, tetanus toxoid, etc. See for example, *Microbiology*, Hoeber Medical Division, Harper and Rowe, 1969; Landsteiner, *Specificity of Serological Reactions*, Dover Publications, New York, 1962; and Williams et al., *Methods in Immunology and Immunochemistry*, Vol. 1, Academic Press, New York, 1967, for descriptions of preparation of polyclonal antisera. In many instances, it will be desired to prepare monoclonal antibodies, where the monoclonal antibodies may be from various mammalian hosts, such as mice, rodents, primates, humans, etc. Description of techniques for preparing monoclonal antibodies may be found in, *Basic and Clinical Immunology*, Stites et al., Eds., Fourth edition, Lange Medical Publications, Los Altos, Calif. and references cited therein.

These antibodies can be used in various ways, depending upon whether they are polyclonal or monoclonal. The polyclonal antibodies can be used to detect polypeptides having the epitopic site(s) associated with the polypeptides or proteins expressed by the X region of the HTLV viruses. Thus, they can detect the presence of any polypeptide which shares one or more epitopic sites of the subject polypeptides. The monoclonal antibodies, by way of contrast, can detect specific sites or can be used in conjunction to demonstrate the presence of two specific epitopic sites. Thus, the monoclonal antibodies provide for greater specificity as to a specific epitopic site or sites present on the same or different polypeptides.

The subject polypeptides, their fusion products, and antibodies specific for the polypeptides find use in a variety of diagnoses for detecting the presence of HTLV viruses or individual types of such viruses. This can be done by employing lysates, fixing cells and employing immunofluorescence, detecting the presence of related antibodies or antigens in serum, or the like.

The polypeptides and/or antibodies may be used without modification or may be modified in a variety of ways, for example, by labeling. By labeling is intended joining, either covalently or non-covalently, a moiety which directly or indirectly provides for a detectable signal. A wide variety of labels are known and have found extensive use in both the scientific and patent literature. These labels include radionuclides, enzymes, substrates, cofactors, inhibitors, fluorescers, chemiluminescers, particles, magnetic particles, and the like. Illustrative patents include Nos. 3,817,837, 3,850,752, 3,939,350, 3,996,345, 4,277,437, 4,275,149 and 4,366,241, which are merely illustrative of various techniques which are available.

The manners for linking the polypeptides to the various labels have been extensively reported in the literature and do not require extensive exemplification here. Many of the techniques involve the use of activated carboxyl groups, either through the use of carbodiimide or active esters to form peptide bonds; the formation of thioethers by reaction of a mercapto group with an activated halogen, e.g., chloroacetyl, or activated olefin, e.g., maleimide, for linkage, or the like.

The assays may be homogeneous (without a separation step between free reagent and receptor-ligand complex) or heterogeneous (with a separation step between free reagent and receptor-ligand complex). Various commercial assays exist, such as radioimmunoassay (RIA), ELISA, EIA, EMIT, SLIFA, and the like.

Unlabeled antibodies can be employed by employing a second antibody which is labeled which recognizes the antibody to a subject polypeptide. These assays have also found extensive exemplification in the literature.

Antibodies to either of the peptides $p40^{xI}$ or $p37^{xII}$ may be used to detect polypeptides of HTLV sharing common epitopic sites. In addition, by employing techniques which allow for molecular weight discrimination, e.g., immunoprecipitation followed by SDS page, the nature of the polypeptide and, therefore, the virus may be further characterized.

Frequently, the reagents are supplied in kits, so as to optimize the sensitivity of the assay. For the subject invention, depending upon the nature of the assay, the protocol, and the label, either labeled or unlabeled antibody, or labeled polypeptide is provided, usually in conjunction with other additives, such as buffer, stabilizers, materials necessary for signal production, e.g., substrates for enzymes, and the like. Desirably, the reagents are provided as a dry powder, where the reagents may be reconstituted in an aqueous medium having appropriate concentrations for performing the assay.

The antibodies can also be used for affinity chromatography in isolating the polypeptide produced by HTLV-I or -II or analogous polypeptides. Columns can be prepared where the antibodies are linked to a solid support, e.g., particles, such as agarose, Sephadex, or the like, where a cell lysate may be passed through the column, the column washed, followed by increasing concentrations of a mild denaturant, e.g., urea, whereby the purified proteins will be released.

The reagents of the present invention may be used to detect antibodies to the X region proteins in patients suspected of being exposed to HTLV and/or suffering from HTLV-related diseases. It has been found by the inventors herein that the presence of anti-X region antibodies in sera shows a higher correlation with HTLV exposure and disease in some cases than the presence of either anti-gag and anti-env antibodies, and such results are set forth in detail in the Experimental section hereinafter.

A wide variety of protocols may be employed for detecting the anti-X region antibodies, normally employing either labeled or unlabeled $p40^{xI}$, $p37^{xII}$, or fragments thereof. For example, a competitive radioimmunoassay could be run where labeled anti-$p40^{xI}$ or anti-$p37^{xII}$ competes with serum antibody for binding to solid phase antigen. Other well known immunoassays, as set forth hereinabove, could also be adapted for the detection of anti-X region antibodies in sera. Other laboratory analyses, such as Western blots, would also be capable of detecting the antibody, but normally are much less convenient than immunoassay techniques for diagnostic screening.

Screening for the x-region antibodies may be combined with screening for other HTLV-related antibodies, particularly anti-gag and anti-env antibodies. As demonstrated in the Experimental section hereinafter, there are some instances where a patient suffering from HTLV-related disease, or exposed to HTLV, will have anti-gag and/or anti-env antibodies but be negative for anti-X region antibodies. Thus, a combined screen for all three antibodies may provide the highest reliability.

EXPERIMENTAL

The following examples are offered by way of illustration and not by way of limitation.

The following amino acid sequences were prepared by conventional synthetic procedures:

Sequence (1): C P E H Q I T W D P I D G R
Sequence (2): I P R L P S F P T Q R T S K T L K
*Sequence (3'): P D P G L R P Q N

*Sequence (3') is located on Sequence (3) of p40$^{xI}$ whose entire sequence is illustrated hereinabove.

Each of the oligopeptides described above was individually linked to keyhole limpet hemocyanin (Lerner et al., Proc. Natl. Acad. Sci. USA (1981) 78:3403, which is incorporated herein by reference) and the resulting immunogens injected into rabbits for production of antisera specific to the oligopeptides. The resulting antisera were isolated in accordance with conventional techniques and used in the following studies.

The SLB-I cell line was derived from normal human adult peripheral blood cells transformed in vitro with HTLV-I (Koeffler et al., Blood (1984) 64:482; Gasson et al., in Normal and Neoplastic Hematopoiesis, Golde, Marks, Eds., Alan Liss, 1983, p. 129). The lysate from the cells were immunoprecipitated as described below. Standard markers were $^{14}$C-labeled protein of 200 kd, 92.6 kd, 68 kd, 43 kd and 25.7 kd. The lanes of the gel were (a) SLB-I cell lysate and preimmune sera; (b) SLB-I cell lysate and anti sequence 1 sera; (c) SLB-I cell lysate and anti sequence 1 sera, which was preincubated for 30 min at 4° C. with 10 μl of 1 mg/ml solution of the sequence I peptide; (d) the standard markers; (e) SLB-I cell lysate and preimmune sera; (f) SLB-I lysate and anti sequence 2 sera; (g) SLB-I cell lysate and anti sequence 2 preincubated with sequence 2 peptide as above; (h) MOLT-4 cell lysate and anti sequence 1 sera; (i) HL-60 cell lysate and anti sequence 1 sera; (j) MOLT-4 cell lysate and anti sequence 2 sera; (k) HL-60 cell lysate and anti sequence 2 sera; (l) SLB-I cell lysate and normal human sera; (m) SLB-I cell lysate in human sera from a patient with adult T-cell lymphoma (HTLV-I-associated).

Total cellular proteins were metabolically labeled with [$^{35}$S]-methionine by culturing cells at a concentration of $1 \times 10^6$ cells/ml in methionine-free Earle's modified minimal essential media (Flow Laboratories, McLean, Va.) supplemented with 2% glutamine, 10% dialysed fetal calf serum in 100 μCi/ml of [$^{35}$S]-methionine (>600 Ci/mmole, Amersham, Arlington Heights, Ill.) at 37° C. for a period of 4–5 hr. The cells were then washed twice in cold (4° C.) phosphate buffered saline, pH 7.4 and lysed at a concentration of $4 \times 10^6$ cells/ml in RIPA buffer (50 mM NaCl, 1% sodium deoxycholate, 1% Triton X-100, 0.1% SDS, 10 mM Tris-HCl, pH 7.2 and 1 mM phenylmethylsulfonyl fluoride). The cell extracts were clarified by centrifugation at 100 kg for 60min at 4° C.

Immunoprecipitation reaction mix consisted of 10 μl of the indicated sera and $8 \times 10^6$ cpm of clarified cell lysate in a final volume of 250 μl of RIPA buffer containing 2 mg/ml BSA and 0.07% SDS. The antigen-antibody reaction was carried out overnight at 4° C. Immunoprecipitates were collected by addition of 60 μl of a 10% suspension of Pansorbin (Calbiochem-Behring, La Jolla, Calif.) for 30 min at 4° C. The samples were then washed four times in RIPA buffer and analyzed on 7.5% SDS-polyacrylamide gels as described by Laemmli, Nature (1970) 227:680. The gels were then subjected to fluorography.

A protein of 40 kd was consistently immunoprecipitated from these cells with antisera directed to either of the sequence 1 or sequence 2 peptides. This protein was not precipitated by preimmune sera and the immunoprecipitation of this protein could be completely competed away with the relevant peptide indicating a specific antigen-antibody reaction. This protein was not found in control hematopoietic cell lines, including a transformed T-cell line which was not infected with HTLV, i.e., MOLT-4 nor observed with HL-60.

The JLB-I cell line was an HTLV-II-transformed T-cell line which was derived from the same normal donor whose cells were used to establish the SLB-I cell line. In these cells, a protein of 37 kd was found using the same antisera as described above, employing the same procedures and controls. A second protein of lower molecular weight, approximately 30 kd, was also identified in the JLB-I cell line using the anti sequence 2 sera. This protein was not recognized by anti sequence 1 sera.

In the next study, HTLV-II-infected B-cells were employed (Chen et al., Nature (1984) 309:276). Immunoprecipitation from uninfected and HTLV-II-infected B cells was investigated. The lanes involved (a) an uninfected cell lysate and anti sequence 1 sera; (b) HTLV-II-infected cell lysate and anti sequence 1 sera; (c) HTLV-II-infected cell lysate and anti sequence 1 sera preincubated with sequence 1 peptide; (d) HTLV-II-infected cell lysate and preimmune sera; (e) uninfected cell lysate and anti sequence 2 sera; (f) HTLV-II cell lysate and anti sequence 2 sera; (g) HTLV-II-infected cell lysate and anti sequence 2 sera preincubated with sequence 2 peptide; and (h) HTLV-II-infected cell lysate and preimmune sera. The 36 kd protein was seen in infected B-cell lysates and not in uninfected cells. Immunoprecipitation of the 36 kd protein found in the HTLV-II-infected B-cells could be competed by preincubation of the antisera with the appropriate synthetic peptide and preimmune sera did not recognize the protein.

Antisera directed against sequence 3' failed to recognize any unique protein in either HTLV-I or -II, which is inconclusive in view of the small size of the peptide.

Restriction fragments from the X region of HTLV-I were cloned and expressed as fusion proteins in E. coli, and the resulting expression products used to immunize rabbits and obtain antisera. The three restriction fragments employed and the corresponding polypeptides were as follows:

(1) MstI-AvaI encoding amino acids 115 through 182 on HTLV-I sequence (5) hereinabove, referred to hereafter as the 68 mer peptide;
(2) ScaI-HincII encoding amino acids 274 through 357 on HTLV-I sequence (5) hereinabove, referred to hereinafter as the 84 mer peptide; and
(3) ScaI-HincII encoding amino acids 304 through 357 on the HTLV-I sequence (5) hereinabove, referred to hereinafter as the 54 mer peptide.

The antibodies produced from each of the peptide fragments were found to be reactive with both the $p40^{xI}$ and $p37^{xII}$ proteins.

Sera from patients suspected of suffering from HTLV-I-induced diseases and from normal individuals were screened for the presence of antibodies to the $p40^{xI}$ protein. Such screening indicated that a high percentage of patients suffering from adult T-cell leukemia (ATL), from chronic ATL, from pre-ATL, and from adult T-cell lymphoma (TL) as well as from apparently disease-free family members of these patients, have antibodies to $p40^{xI}$ in their sera.

Sera from the following groups were tested:
(a) Acute ATL: characterized by elevated WBC, diffuse lymphadenopathy, hepatosplenomegaly, skin lesions, and frequently, hypercalcemia. These patients usually have significant immunosuppression and succumb to their disease within 18 months.
(b) TL: clinical course as above except there are no circulating malignant cells, i.e., normal to low WBC.
(c) Chronic ATL: characterized by an elevated WBC with mild lymphadenopathy and signs of mild to moderate immunosuppression and a more chronic course of disease.
(d) Pre-ATL: characterized by normal total WBC with abnormal circulating cells.
(e) Family members of patients, including spouses, siblings and children.

The testing of the sera was accomplished by liquid phase immunoprecipitation. Briefly, HTLV-I infected cells were incubated with $^{35}$S-methionine and lysed. The cellular lysates, including labelled X, gag, and env proteins, were then combined with sera from the above patient groups as well as with anti-$p40^{xI}$ prepared in the laboratory as a positive control. After incubating overnight, the antibody-antigen complexes formed were precipitated with *Staphylococcus aureus,* and the resulting pellets washed to remove non-specifically bound substances. The remaining pellet was dissociated by boiling in a mercaptoethanol-sodium dodecylsulfate solution, and centrifuged to remove the bacterial cells. The supernatants, containing the dissociated antibodies and antigens, were then run on a polyacrylamide gel, where only the labeled antigens were detectable by autoradiography. The X, gag, and env proteins were distinguished on the basis of size. The results are set forth in Table I.

TABLE I

| Disease/Patient No. | Antibodies Present in Sera | | |
|---|---|---|---|
| | anti-x | anti-gag | anti-env |
| ATL | | | |
| 1 | ++ | 0 | + |
| 2 | ++ | 0 | + |
| 3 | 0 | 0 | + |
| 4 | + | + | +++ |
| 5 | + | + | + |
| 6 | ++ | + | +++ |
| 7 | + | 0 | + |
| 8 | ++++ | 0 | + |
| 9 | ++ | + | + |
| 10 | + | 0 | + |
| 11 | + | 0 | + |
| 12 | ++ | 0 | + |
| 13 | + | 0 | + |
| 14 | + | 0 | 0 |
| 15 | + | ++ | ++ |
| 16 | +++ | + | + |
| 17 | 0 | ++ | +++ |
| 18 | 0 | 0 | 0 |
| 19 | + | 0 | 0 |
| 20 | + | 0 | 0 |
| 21 | ++++ | +++ | ++ |
| 22 | + | 0 | 0 |
| 23 | ++ | + | + |
| 24 | + | + | + |
| 25 | ++ | ++ | ++ |
| 26 | + | +++ | ++ |
| 27 | 0 | 0 | 0 |
| 28 | + | + | + |
| 29 | +++ | ++ | ++ |
| 30 | + | 0 | 0 |
| TL | | | |
| 1 | + | +++ | ++++ |
| 2 | +++ | + | +++ |
| 3 | ++ | ++ | ++ |
| Pre-ATL | | | |
| 1 | + | ++ | 0 |
| 2 | ++ | ++ | ++++ |
| 3 | + | + | + |
| 4 | +++ | 0 | ++ |
| 5 | ++ | + | + |
| 6 | 0 | ++ | ++ |
| 7 | 0 | +++ | ++ |
| 8 | 0 | 0 | 0 |
| 9 | 0 | ++ | ++ |
| 10 | + | +++ | ++ |
| 11 | + | 0 | 0 |
| 12 | 0 | ++ | 0 |
| 13 | 0 | +++ | ++++ |
| 14 | ++++ | ++ | + |
| 15 | 0 | + | + |
| 16 | + | 0 | + |
| Chronic ATL | | | |
| 1 | ++++ | ++ | +++ |
| 2 | + | ++ | + |
| 3 | ++++ | + | 0 |
| 4 | 0 | 0 | 0 |
| Potential Carriers | | | |
| 1 | + | 0 | + |
| 2 | +++ | 0 | + |
| 3 | + | 0 | + |
| 4 | ++ | + | ++ |
| 5 | +++ | + | ++ |
| 6 | ++++ | ++ | ++ |
| 7 | +++ | + | + |
| 8 | ++ | 0 | + |
| 9 | ++++ | + | + |
| 10 | 0 | 0 | + |
| 11 | ++ | + | 0 |
| 12 | + | +++ | +++ |
| 13 | ++ | + | + |
| 14 | 0 | 0 | 0 |
| 15 | + | 0 | 0 |
| 16 | +++ | + | 0 |
| 17 | 0 | 0 | 0 |
| 18 | 0 | 0 | 0 |
| 19 | ++++ | ++ | + |
| 20 | + | + | 0 |
| 21 | 0 | +++ | +++ |
| 22 | ++ | + | 0 |
| 23 | ++ | + | ++ |
| 24 | ++ | + | 0 |
| 25 | +++ | 0 | 0 |
| 26 | 0 | 0 | 0 |
| 27 | ++ | + | 0 |
| 28 | +++ | + | + |

TABLE I-continued

| Disease/ | Antibodies Present in Sera | | |
|---|---|---|---|
| Patient No. | anti-x | anti-gag | anti-env |
| 29 | ++++ | + | ++ |
| 30 | + | ++ | ++ |

Overall, of the 53 patients with HTLV-I associated disease, 41 (77%) had detectable levels of antibodies to the p40$^{xI}$ protein as determined in the liquid phase immunoprecipitation assay. In 30 potential carriers, 24 (80%) had detectable antibodies to p40$^{xI}$. For both the patients and family members, the observed levels of anti-p40$^{xI}$ antibody frequency exceeded the levels of anti-gag or anti-env antibody. Assuming the amount of antigen in the assay is not rate limiting, the observed level (intensity of observed band on the gel) of the antibody will depend on the amount and the affinity/avidity of the antibody in the serum sample. A summary of the data follows.

Of 30 patients with ATL, 26 (87%) had detectable antibody to p40$^{xI}$. In 14 patients (47%) the levels of anti-X antibody exceeded the levels of both anti-gag and anti-env antibodies. In 19 patients (63%) the level of anti-X antibody exceeded the level of either anti-gag or anti-env antibodies. In 5 patients (17%) anti-X antibody was the only antibody detected. In only 5 patients (17%) was the level of anti-X antibody exceeded by the level of either anti-gag or anti-env antibodies. In only 4 patients (13%) no anti-X antibody was detected. Of 3 patients with TL, all (100%) had detectable levels of anti-X antibody and in 1 patient the level of anti-X antibody was greater than the level anti-gag antibody. Of 16 patients with pre-ATL, 9 (56%) had detectable levels of anti-X antibody. Of 4 patients with chronic ATL, 3 (75%) had detectable levels of anti-X antibody. The level of antibodies was greater than that of both anti-gag and anti-env antibodies in 2 of the patients. Of 30 family members who had no overt evidence of disease, but were suspected carriers, 24 (80%) had detectable antibodies to the p40$^{xI}$ protein. In 17 patients (56%) the levels of anti-X antibody exceeded the levels of anti-gag or anti-env antibody.

These data indicate that patients infected with HTLV-I, as well as suspected carriers of HTLV-I, do produce antibody to the p40$^{xI}$ gene product and that detection of these antibodies may serve as a potential diagnostic test for exposure to HTLV-I. In particular, the data indicate that sometimes detection of anti-X antibodies is more reliably associated with HTLV-I infection than the detection of either anti-gag or anti-env antibodies. In patients suffering from ATL, only four sera tested negative for anti-X, while 16 sera tested negative for anti-gag and 7 sera tested negative for anti-env. Conversely, only one ATL patient was positive for anti-gag and anti-env who was negative for anti-X and only 2 ATL patients were positive for anti-gag or anti-env and negative for anti-X. For the highest reliability, it might be best to assay for all three antibodies in a clinical assay for HTLV-I disease.

It is evident from the above results, that proteins specific for HTLV-I and HTLV-II are expressed by sequences found in the X region of the respective viruses. Antibodies prepared in accordance with the subject invention provide for the detection of such sequences, as well as the determination of the presence of HTLV viruses and which of the viruses is present. In addition, the antibodies, polypeptides and recognized proteins may be used as reagents for the detection of the individual viruses and the determination of the nature of infection and the etiology of tumor formation.

Although the foregoing invention has been described in some detail by way of illustration and example for purposes of clarity of understanding, it will be obvious that certain changes and modifications may be practiced within the scope of the appended claims.

What is claimed is:

1. A polypeptide comprising:
    at least 12 amino acids wherein the sequence of said polypeptide includes an epitopic site and wherein said sequence is substantially the same as a sequence from a peptide expressed by an HTLV-I virus or an HTLV-II virus with the proviso that the sequence of said polypeptide is other than the entire native sequence of a 42 kD expression product of the X-region of HTLV-I and comprises at least one of the following sequences or a part thereof:

Sequence (1): C P E H Q (aa)$^A$ T W D P I D G R,
    Sequence (2): I P R L P S F P T Q R T S (aa)$^B$ T L K,
    Sequence (3): K(aa)$^{ArB}$ (aa)$^{Ah}$ P (aa)$^{Ar}$ RNG (aa)$^{ArS}$ (aa)$^{AS}$ EPTLG (aa)$^{AcAm}$ (aa)$^{AmB}$ LP (aa)$^{Ah}$ L (aa)$^{AAh}$ FP (aa)$^{Ac}$ PGLRPQN (aa)$^A$ YT (aa)$^{AAh}$ WG (aa)$^{AB}$ (aa)$^{Ah}$ VVC (aa)$^{AS}$ YLYQLSPP (aa)$^{AS}$ TWPL (aa)$^A$ PHVIFCHP (aa)$^{AB}$ Q, and
    Sequence (4): V (aa)$^A$ QSS (aa)$^{AAh}$ (aa)$^{AAr}$ IF (aa)$^{AcB}$ KF (aa)$^{AcAm}$ TKA (aa)$^{Ar}$ HPS (aa)$^{Ar}$ LLSH (aa)$^{AAm}$ LIQY SSFH (aa)$^{AhAm}$ LHLLF (aa)$^{Ac}$ EYTNIP (aa)$^A$ S (aa)$^A$ LFN (aa)$^{AcB}$ (aa)$^{AcB}$ EADDN (aa)$^{AAc}$ (aa)$^{AcB}$ EPQISPGGLEPPSEKH FRETEV wherein (aa)$^A$, (aa)$^{Ac}$, (aa)$^{Ah}$, (aa)$^{Am}$, (aa)$^{Ar}$, (aa)$^B$, (aa)$^{ArB}$, (aa)$^{ArS}$, (aa)$^{AS}$, (aa)$^{AcAm}$, (aa)$^{AmB}$, (aa)$^{AAh}$, (aa)$^{AB}$, (aa)$^{AAr}$, (aa)$^{AcB}$, (aa)$^{AhAm}$, (aa)$^{AAc}$, and (aa)$^S$ may be the same or different and are selected from any one of the twenty naturally occurring amino acids found in proteins, and wherein superscript A designates an aliphatic amino acid, superscript Ac designates an acidic amino acid, superscript Ah designates an amino acid having an aliphatic-hydroxyl side chain, superscript Am designates an amino acid having an amine-containing side chain, superscript Ar designates aromatic amino acid, superscript B designates a basic amino acid, superscript S designates an amino acid having a sulfur-containing side chain, and combinations of two superscripts indicate amino acids that may be from any of the amino acids designated by either superscript.

2. A polypeptide according to claim 1, wherein said polypeptide comprises any one of:
    sequence (1) and sequence (2) joined by an amino acid sequence of from 5 to 12 amino acids;
    sequence (3) and sequence (4) joined by an amino acid sequence of from 20 to 200 amino acids; and
    sequence (2) and sequence (3) joined by an amino acid sequence of from 10 to 30 amino acids.

3. A polypeptide consisting of the amino acid sequence IPRLPSFPTQRTSKTLK.

4. A polypeptide consisting of the amino acid sequence VLQSSSFIFH KFQTKAYHPS FLLSHGLIQY SSFHSLHLLF EEYTNIPISL LFNEKEADDN DHEPQISPGG LEPPSEKHFR ETEV.

5. A polypeptide consisting of the amino acid sequence SSFHSLHL LFEEYTNIPI SLLFNEKEAD DNDHEPQISP GGLEPPSEKH FRETEV.

6. A polypeptide consisting of the amino acid sequence KYSPFRNGYM EPTLGQHLPT LSFPDPGLRP QNLYTLWGGS VVCMYLYQLS PPITWPLLPH VIFCHDGQ.

7. A polypeptide consisting of the amino acid sequence CPEHQITWDPIDGR.

8. Antibodies prepared in response to a polypeptide according to any one of claims 1, 3, 4, 5, 6, or 2, or a polypeptide according to claim 7 joined to an immunogen wherein said antibodies are capable of binding to said polypeptide and to a polypeptide having sequence homology with at least a portion of the expression product of the X region of HTLV-I or HTLV-II, said antibodies being substantially free of other blood proteins.

9. A method for detecting the presence of an HTLV-I or HTLV-II virus which comprises contacting a body fluid from a patient suspected of being exposed to HTLV-I or HTLV-II with an antibody of claim 8 and determining the level of binding of said antibody to protein containing cells or cellular products in said body fluid to form complex as indicative of the presence of HTLV-I or HTLV-II.

10. Antibodies according to claim 8, which are polyclonal antibodies.

11. Antibodies according to claim 8, which are monoclonal antibodies.

12. A method for detecting the presence of HTLV-I or HTLV-II, which comprises combining a protein containing cell part from a cell suspected of being infected with HTLV-I or HTLV-II with an antibody according to claim 11; and determining the presence of a complex formed between said antibody and an HTLV-I or HTLV-II polypeptide as indicative of the presence of HTLV-I or HTLV-II.

13. A method according to claim 12, where the molecular weight of the polypeptide binding to said antibody is determined to distinguish between HTLV-I and HTLV-II.

14. A method according to claim 12, wherein said complex comprises an HTLV-I polypeptide.

15. A method according to claim 12, wherein said complex comprises an HTLV-II polypeptide.

16. A method according to claim 9, wherein said virus is HTLV-I.

17. A method according to claim 9, wherein said virus is HTLV-II.

18. A method according to claim 9, wherein the body fluid is selected from the group consisting of serum, saliva, and semen.

19. A method of detecting the presence of HTLV-I or HTLV-II virus which comprises contacting a body fluid from a patient suspected of containing antibody to HTLV-I or HTLV-II with an antigenic polypeptide in accordance with any of claims 1, 7, 3, or 2 and determining complex formation of said antibody to said antigenic polypeptide as indicative of the presence of HTLV-I or HTLV-II.

20. A polypeptide according to claim 1 or 2, wherein said polypeptide has at least about 95% w/w purity.

21. A polypeptide having an amino acid sequence of at least 12 amino acids within one of the following polypeptide sequences:

Sequence (1): C P E H Q (aa)$^{A}$ T W D P I D G R

Sequence (2): I P R L P S F P T Q R T S (aa)$^{B}$ T L K

Sequence (3): K(aa)$^{ArB}$ (aa)$^{Ah}$ P (aa)$^{Ar}$ RNG (aa)$^{ArS}$ (aa)$^{AS}$ EPTLG (aa)$^{AcAm}$ (aa)$^{AmB}$ LP (aa)$^{Ah}$ L (aa)$^{AAh}$ FP (aa)$^{Ac}$ PGLRPQN (aa) YT (aa)$^{AAh}$ WG (aa)$^{AB}$ (aa)$^{Ah}$ VVC (aa)$^{AS}$ YLYQLSPP (aa)$^{AS}$ TWPL (aa) PHVIFCHP (aa)$^{AB}$ Q Sequence (4): V (aa)$^{A}$ QSS (aa)$^{AAh}$ (aa)$^{AAr}$ IF (aa)$^{AcB}$ KF (aa)$^{AcAm}$ TKA (aa)$^{Ar}$ HPS (aa)$^{Ar}$ LLSH (aa)$^{AAm}$ LIQY SSFH (aa)$^{AhAm}$ LHLLF (aa)$^{Ac}$ EYTNIP (aa)$^{A}$ S (aa)$^{A}$ LFN (aa)$^{AcB}$ (aa)$^{AcB}$ EADDN (aa)$^{AAc}$ (aa)$^{AcB}$ EPQLSPGGLEPPSEKH FRETEV wherein (aa)$^{A}$, (aa)$^{Ac}$, (aa)$^{Ah}$, (aa)$^{Am}$, (aa)$^{Ar}$, (aa), (aa)$^{ArB}$, (aa)$^{ArS}$, (aa)$^{AS}$, (aa)$^{AcAm}$, (aa)$^{AmB}$, (aa)$^{AAh}$, (aa)$^{AB}$, (aa)$^{AAr}$, (aa)$^{AcB}$, (aa)$^{AhAm}$, (aa)$^{AAc}$, and (aa)$^{S}$ may be the same or different and are selected from any one of the twenty naturally occurring amino acids found in proteins, wherein superscript A designates an aliphatic amino acid, superscript Ac designates an acidic amino acid, superscript Ah designates an amino acid having an aliphatic-hydroxyl side chain, superscript Am designates an amino acid having an amine-containing side chain, superscript Ar designates aromatic amino acid, superscript B designates a basic amino acid, superscript S designates an amino acid having a sulfur-containing side chain, and combinations of two superscripts indicate amino acids that may be from any of the amino acids designated by either superscript, and wherein said sequence defines an immunogenic site for antibody recognition and is substantially the same as the amino acid sequence of a polypeptide expressed by a gene which is present, at least in part, in the X region of an HTLV-I or HTLV-II virus with the proviso that the sequence of said polypeptide in other than the entire native sequence of a 42 kD expression product of the X-region of HTLV-I.

22. A polypeptide according to claim 21, having a label providing directly or indirectly a detectable signal.

23. A polypeptide according to claim 22, wherein said label is a radionuclide.

24. A method for determining whether a patient has been exposed to HTLV-I or HTLV-II said method comprising the step of detecting the presence of antibody to a protein expressed from the X region of an HTLV virus in a serum sample from the patient using a polypeptide according to any one of claims 1, 7, 3 or 2 for said detecting.

25. A method as in claim 24, wherein said protein is $p40^{xI}$.

26. A method as in claim 24, further comprising the additional step of the detection of anti-gag or anti-env antibodies in the serum sample by detecting complex formation between said anti-gag or anti-env antibodies and gag or env proteins or fragments thereof.

27. A method according to claim 24, wherein said protein is $p37^{xII}$.

* * * * *